US007439493B2

(12) United States Patent
Teppaz et al.

(10) Patent No.: US 7,439,493 B2
(45) Date of Patent: Oct. 21, 2008

(54) MULTIMODALITY IMAGING PHANTOM AND PROCESS FOR MANUFACTURING SAID PHANTOM

(75) Inventors: Pierre Teppaz, Jacob-Bellecombette (FR); Salah Dine Qanadli, Ville Mont-Royal (CA); Guy Cloutier, LeGardeur (CA); Gilles Soulez, Outremont (CA); Richard Cimon, Rosemère (CA); Louis-Gilles Durand, St-Jean-de-Matha (CA)

(73) Assignees: Institut de Recherches Cliniques, Montreal, Quebec (CA); Centre Hospitalier de l'Universite, Montreal, Quebec (CA); Universite de Montreal, Montreal, Quebec (CA)

( * ) Notice: Subject to any disclaimer, the term of this patent is extended or adjusted under 35 U.S.C. 154(b) by 877 days.

(21) Appl. No.: 10/495,407

(22) PCT Filed: Nov. 5, 2002

(86) PCT No.: PCT/CA02/01633

§ 371 (c)(1),
(2), (4) Date: Nov. 19, 2004

(87) PCT Pub. No.: WO03/040745

PCT Pub. Date: May 15, 2003

(65) Prior Publication Data

US 2005/0123178 A1    Jun. 9, 2005

(51) Int. Cl.
*G01D 18/00* (2006.01)
(52) U.S. Cl. .................... 250/252.1; 250/505.1; 378/18; 378/207; 600/407
(58) Field of Classification Search ........................ None
See application file for complete search history.

(56) References Cited

U.S. PATENT DOCUMENTS 4,331,021 A    5/1982    Lopez et al. .................... 73/1

(Continued)

FOREIGN PATENT DOCUMENTS

EP    1062911 A2    12/2000

OTHER PUBLICATIONS

Bendib K. et al. "Caractérisation of d'une sténose artérielle par imagerie 3D", *Journal de Radiologie*, 80: 1561-1567, (1999).

(Continued)

*Primary Examiner*—David P. Porta
*Assistant Examiner*—Yara B Green
(74) *Attorney, Agent, or Firm*—Myers Bigel Sibley & Sajovec, PA

(57) ABSTRACT

A multimodality imaging phantom is disclosed which is useful for calibrating devices for imaging vascular conduits. The phantom is compatible with X-ray, ultrasound and magnetic resonance imaging techniques. It allows testing, calibration, and inter-modality comparative study of imaging devices, in static or dynamic flow conditions. It also provides a geometric reference for evaluation of accuracy of imaging devices. The tissue-mimicking material is preferably an agar-based solidified gel. A vessel of known desired geometry runs throughout the gel and is connected to an inlet and outlet at its extremities for generating a flow circulation in the vessel. Said phantom also contains fiducial markers detectable in the above-mentioned modalities. The markers are preferably made of glass and are embedded in a layer of agar gel containing a fat component. The markers are implanted at precise known locations to allow identification and orientation of plane views, and they can be used for calibration, resealing and fusion of 3D images obtained from different modalities, and 3D image reconstruction from angiographic plane views. Also disclosed is a process for manufacturing said phantom.

23 Claims, 13 Drawing Sheets

U.S. PATENT DOCUMENTS

| | | | | |
|---|---|---|---|---|
| 4,499,375 | A | 2/1985 | Jaszczak | 250/252.1 |
| 4,551,678 | A | 11/1985 | Morgan et al. | 324/300 |
| 4,644,276 | A | 2/1987 | Sierocuk et al. | 324/307 |
| 4,724,110 | A | 2/1988 | Arnold | 264/102 |
| 4,794,631 | A | 12/1988 | Ridge | 378/207 |
| 4,843,866 | A | 7/1989 | Madsen et al. | 73/1 |
| 4,985,906 | A | 1/1991 | Arnold | 378/18 |
| 5,312,755 | A | 5/1994 | Madsen et al. | 436/8 |
| 5,560,242 | A | 10/1996 | Flax | 73/1 |
| 5,793,835 | A | 8/1998 | Blanck | 378/4 |
| 6,635,486 | B2 * | 10/2003 | Madsen et al. | 436/8 |

OTHER PUBLICATIONS

Blechinger, J.C. et al. "Tissue-Mimicking Gelatin-Agar Gels for Use in Magnetic Resonance Imaging Phantoms", *Medical Physics* 15(4): 629-635, (1988).

Creasy, J.L. et al. "Design and Evaluation of a Flow Phantom", *Academic Radiology*, 2:902-904, (1995).

Dabrowski, W. et al. "a Real Vessel Phantom for Imaging Experimentation", *Medical Physics* 24(5): 687-693, (1997).

De Poorter, J. et al. "The Proton-Resonance-Frequency-Shift Method Compared with Molecular Diffusion for Quantitative Measurement of Two-Dimensional Time-Dependent Temperature Distribution in a Phantom", *Journal of Magnetic Resonance*, Series B, 103(3): 234-241, (1994).

Fahrig, R. et al. "A Three-Dimensional Cerebrovascular Flow Phantom", *Medical Physics* (1999).

Frayne, Richard et al. "A Geometrically Accurate Vascular Phantom for Comparative Studies of X-Ray, Ultrasound, and Magnetic Resonance Vascular Imaging: Construction and Geometrical Verification", *Medical Physics* 20(2), Pt. 1, (1993).

Hill, D LG "Combination of 3D Medical Images from Multiple Modalities", Thesis submitted for the degree of doctor of philosophy of the University of London (1993).

International Search Report, corresponding to Application PCT/CA02/01633, mailed on Apr. 3, 2003.

Kerber, Charles W. et al. "Flow Dynamics in the Human Carotid Artery: I. Preliminary Observations Using a Transparent Elastic Model", *American Journal of Neuroradiology* 13(1):173-180, (1992).

Rickey, D.W. et al. "A Wall-Less Vessel Phantom for Doppler Ultrasound Studies", *Ultrasound in Med. & Biol.*, 21(9): 1163-1176, (1995).

Smith, R.F. et al. "Stenosed Anthropomorphic Vascular Phantoms for Digital Subtraction angiography, Magnetic Resonsance and Doppler Ultrasound Investigations", *Physics of Medical Imaging* SPIE 2163: 235-242 (1994).

* cited by examiner

MULTIMODALITY IMAGING PHANTOM AND PROCESS FOR MANUFACTURING SAID PHANTOM

RELATED APPLICATIONS

This application claims priority under 35 U.S.C. § 371 from PCT Application No. PCT/CA02/01633, filed in English on Nov. 5, 2002, which claims the benefit of U.S. application Ser. No. 10/010,886, filed Nov. 8, 2001, now abandoned, the disclosures of which are incorporated by reference herein in their entireties.

FIELD OF THE INVENTION

The present invention relates to a multimodality imaging phantom and a process for manufacturing the same. The multimodality imaging phantom is particularly useful for calibrating imaging devices or apparatuses using different imaging modalities.

BACKGROUND OF THE INVENTION

Several medical imaging techniques are now currently in use to investigate the severity of vascular diseases (i.e. quantification of the vascular lumen geometry) and enable clinicians to detect stenoses, thromboses, development of collateral vessels, aneurysms, or malformations. The techniques are based either on X-rays (X-ray angiography, and computerized tomography (CT)), ultrasonography (B-mode, M-mode, pulsed-wave Doppler, power Doppler, color Doppler, intravascular ultrasound (IVUS)), or on magnetic resonance angiography (MRA) (gradient-recalled echo sequence, phase-contrast, gadolinium enhanced angiography). Angiography (MRA) provides geometrical data on the vessel lumen, whereas IVUS and CT can be used independently or complementary to angiography to investigate the arterial wall morphology and composition. Knowledge on the hemodynamics is also of great interest to evaluate the consequences of lesions on blood supply to the tissues perfused by diseased vessels. Doppler ultrasound and phase contrast MRA allow to study blood flow, namely to measure blood velocities in the vessels. As the precise quantification of morphological and hemodynamic parameters is the basis of the clinical diagnosis, calibration of the medical imaging apparatuses is an essential step required for accurate imaging and evaluation of blood vessels. Test objects, known as calibration phantoms, are commonly used for this purpose and specific phantoms have been developed to meet the requirements associated to each imaging modality.

Even after calibration, no imaging technique is error free. In the literature, plane X-ray angiography is considered as the gold standard (Bendib K., Poirier C., Croisille P., Roux J. P., Revel D., and Amiel M.—Caractérisation d'une sténose artérielle par imagerie 3D, Journal de Radiologie, 1999, 80:1561-1567) for the evaluation of arterial diseases, because it is the technique with the best spatial resolution. Nevertheless, other techniques, especially those allowing 3D imaging, bring important additional information concerning the morphology, the severity, and the location of the lesion. This is why comparative studies of imaging techniques, in the same experimental conditions, are necessary to assess the accuracy and determine the advantages and limitations of each one. Moreover, a gold standard, different from the tested techniques, should be available for precise assessment.

Vascular flow phantoms are ideal tools for such studies since they provide a way of testing the geometric accuracy, with easy reproducibility of the experimental conditions when different modalities are tested. They can also be used to compare the blood flow velocity patterns obtained by ultrasound and MRA. Moreover, it is possible to reproduce vascular pathologies, with a known geometry that can be accurately determined during fabrication, and which can be used as the "gold standard reference" for evaluation of imaging devices. Multimodality phantoms have to meet three major requirements. First, they must be compatible with many if not all the imaging modalities evaluated, i.e. it is necessary that the vessel position can be clearly identified on the images, with no or minimum artifacts in any modality. Second, they should be anthropomorphic, i.e. their geometry should mimic as close as possible the complexity of real human vessels. Finally, they should contain markers visible in all modalities for image calibration, resealing and fusion.

Multimodality anthropomorphic vascular flow phantoms have been proposed in the recent years using three major techniques: stereolithography, phantoms including real vessels and lost-material casting method. For instance, Creasy et al. (Creasy J. L., Crump D. B., Knox K., Kerber C. W., and Price R. R.—Design and Evaluation of a Flow Phantom, Academic radiology, 1995, 2:902-904) presented a simple cranial blood flow phantom compatible with X-ray, MRA and CT angiography. It consisted in an acrylic skull filled with a silicone polymer mimicking human brain tissue, which contains the main cerebral vessels. Arteries were modeled from actual human arteries by injecting fresh cadaver arteries with acrylic resin. Veins were constructed in wax using resin cast human model duplicating dimensions and shape of actual cerebral human veins. When the vein and artery models were placed and the skull filled with silicon polymer, wax was removed thermally and chemically. Fahrig et al. (Fahrig R., Nikolov H., Fox A. J., and Holdsworth D. W.—A Three-Dimensional Cerebrovascular Flow Phantom, Medical Physics, 1999, 26(8):1589-1599) constructed a three-dimensional cerebrovascular flow phantom compatible with X-ray angiography, MRA and CT techniques using data taken from the literature and a casting method similar to that described above and cerrolow 117 as the casting material. The authors tested the phantom for geometric accuracy using high resolution MRA and CT protocols. Their results showed good agreement (within 4%) between the arterial diameters determined from the radiographic images and those measured on cerrolow cores before their implantation.

To solve the problem of realistic anthropomorphic geometry, including diseased segments, studies have been made on phantoms derived from real vessels harvested on cadavers (Kerber C. W., and Heilman C. B.—Flow Dynamics in the Human Carotid Artery: I. Preliminary Observations Using a Transparent Elastic Model, American Journal of Neuroradiology, 1992, 13:173-180). Dabrowski et al. (Dabrowski W., Dunmore-Buyze J., Rankin R. N., Holdsworth D. W., and Fenster A.—A real vessel phantom for imaging experimentation, Medical Physics, 1997, 24(5):687-693) used a human abdominal aorta, fixed with a 10% formaldehyde solution at 90 mmHg to preserve its geometry, to perform comparisons of X-ray angiography, CT scan and 3D B-mode ultrasound. The images obtained from the three modalities could be compared with each other and showed good overall correlation. These real vessel phantoms had two limitations: first, the geometry of the artery was not known a priori, and thus, there was no gold standard to assess the accuracy of the imaging devices. Second, the geometry of each artery was unique and could not be duplicated if the vessel was damaged.

Frayne et al. (Frayne R., Gowman L. M., Rickey D. W., Holdsworth D. W., Picot P. A., Drangova M., Chu K. C., Caldwell C. B., Fenster A., and Rutt B. K.—A Geometrically Accurate Vascular Phantom for Comparative Studies of X-Ray, Ultrasound, and Magnetic Resonance Vascular Imaging: Construction and Geometrical Verification, Medical Physics, 1993, 20(2):415-425) built a flow phantom of the human carotid bifurcation based on geometrical data taken from the literature by using a thin-walled polyester-resin replica of the carotid bifurcation surrounded by an agar tissue-mimicking material (lost-material casting technique). The two-parts mold was machined in blocks of acrylic using a numerical milling machine and the casting material was wax. The blood- and tissue-mimicking materials had X-ray, ultrasound and MRA properties close to those of blood and human tissues, but polyester resin was found to be a poor ultrasound and MRA tissue-mimicking material. Static images were recorded with X-ray angiography, CT, ultrasound and MRA for evaluation of the geometric accuracy of these techniques. Velocity images were acquired under steady flow with color Doppler and phase contrast MRA. The two techniques gave flow patterns which qualitatively agreed with each other and with literature data, and measured volume flow-rates were in good agreement (4.4%) with actual values.

Smith et al. (Smith R. F., Frayne R., Moreau M., Rutt B. K., Fenster A., and Holdsworth D. W.—Stenosed Anthropomorphic Vascular Phantoms for Digital Substraction Angiography, Magnetic Resonance and Doppler Ultrasound Investigations, SPIE Physics of medical imaging, 1994, 2163:235-242) improved the method proposed by Frayne et al. (1993) by using aluminum molds, replacing wax with cerrobend 158 and agar gel with a polyester resin. A drawback of this method is the absence of tissue-mimicking material around the vessel, which has implications in MRA and ultrasound images. Recently, Bendib et al. (1999) used vascular phantoms to compare the accuracy of MRA, CT angiography and 3D X-ray digital substraction angiography for evaluation of stenoses using stereolithography. One limitation of stereolithography is that it only allows fabrication of rigid-wall phantoms, and the type of materials that can be used is limited. Moreover, the lumen of the vessel is not perfectly smooth (Fahrig et al., 1999). The phantoms were filled with contrast agents compatible with each imaging modality, but there was no fluid circulation. The authors found that among the three methods tested, 3D X-ray angiography was more accurate than MRA and CT for the evaluation of the degree, the shape and the location of stenoses.

Also known in the art, there are the following U.S. Pat. Nos. 4,331,021; 4,499,375; 4,551,678; 4,644,276; 4,724,110; 4,794,631; 4,843,866; 4,985,906; 5,312,755; 5,560,242; and 5,793,835.

However, all of these patents describe apparatus and methods that are each limited to a single mode of imaging.

There is a need for a phantom using different modes of imaging like X-ray, ultrasound and magnetic resonance (MR) to calibrate apparatuses.

SUMMARY OF THE INVENTION

An object of the invention is to provide a multimodality imaging phantom for calibrating an imaging apparatus.

Another object of the invention is to provide a process for manufacturing a multimodality imaging phantom for calibrating an imaging apparatus.

The multimodality imaging phantom provided by the present invention is for calibrating an imaging apparatus and comprises:

a container having walls allowing a use of the imaging apparatus for imaging the interior thereof, the walls being provided with an inlet and an outlet;

a first layer of tissue mimicking material located in a portion of the interior of the container;

at least one marker embedded in the first layer, the at least one marker having an acoustic impedance that is 3 to 30 times higher than that of the first layer, an X-ray absorption coefficient that is 3 to 50 times higher than that of the first layer, and a MR axial relaxation time that is 2 to 20 times lower than that of the first layer; and a second layer of tissue mimicking material located in a remaining portion of the interior, the second layer embedding a vessel operatively connected to the inlet and the outlet.

The process provided by the present invention is for manufacturing a multimodality imaging phantom for calibrating an imaging apparatus, and comprises the steps of:

a) providing a container having walls allowing a use of the imaging apparatus for imaging the interior thereof, the walls being provided with an inlet and an outlet;

b) providing a first layer containing a first tissue mimicking material in a portion of the interior of the container;

c) embedding at least one marker in the first layer, the at least one marker having an acoustic impedance that is 5 to 20 times higher than that of the first layer, an X-ray absorption coefficient that is 3 to 50 times higher than that of the first layer, and a MR axial relaxation time that is 2 to 10 times lower than that of the first layer;

d) providing a second layer containing a second tissue mimicking material in the remaining portion of the interior of the container; and e) embedding a vessel in the second layer, the vessel being operatively connected to the inlet and the outlet of the container.

The invention and its process of manufacture will be better understood upon reading the following non restrictive description of a preferred embodiment thereof, made with references to the accompanying drawings.

DESCRIPTION OF PREFERRED EMBODIMENTS OF THE INVENTION

Figure 1:
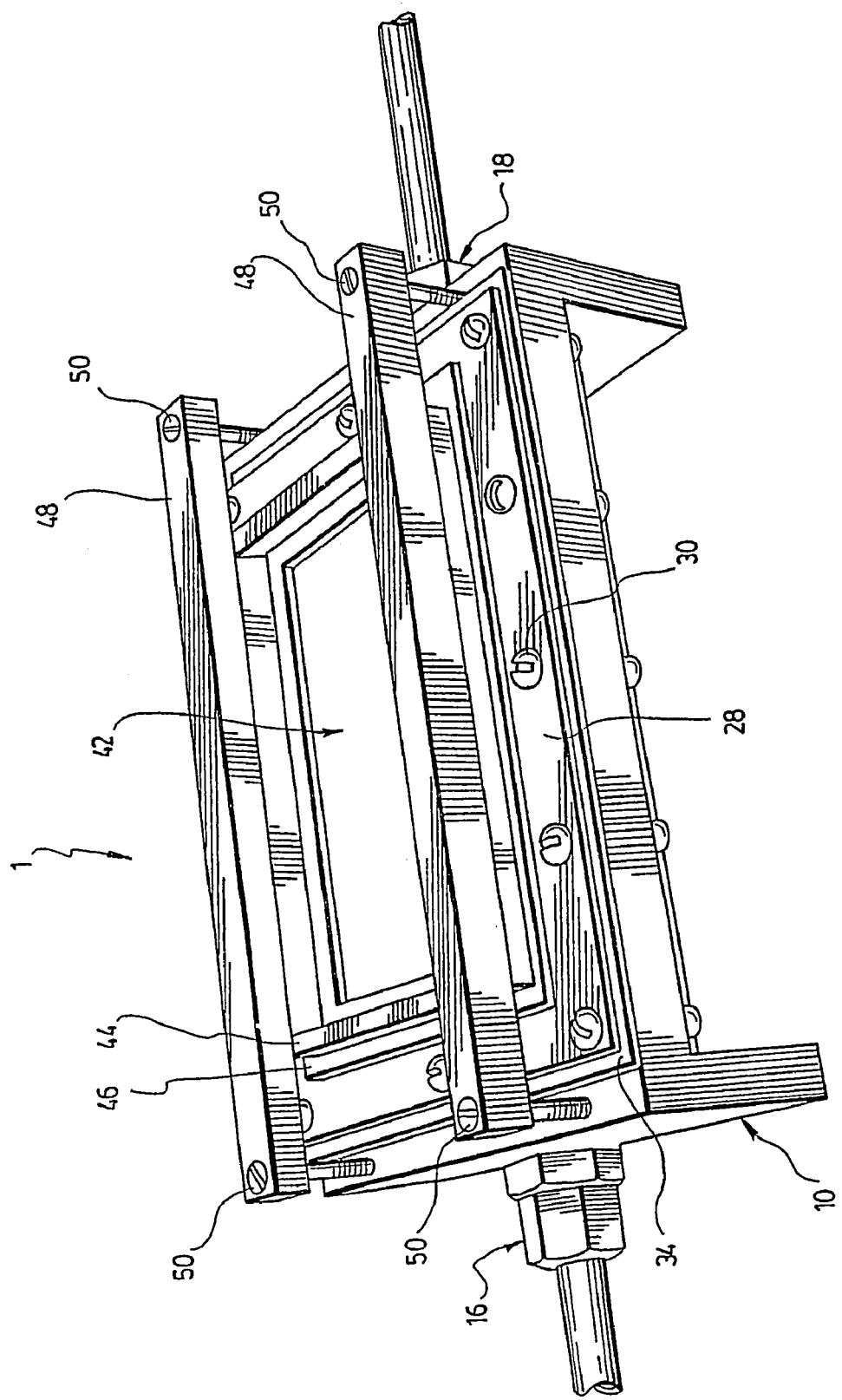
FIG. 1 is a perspective view of a multimodality imaging phantom according to the invention.

The present invention is directed to a multimodality imaging phantom for calibrating an imaging apparatus, and more preferably, the apparatus uses one of the following imaging modalities: ultrasonography, X-ray angiography, X-ray computed tomography and magnetic resonance imaging.

As shown in FIGS. 1, 2, 3, 4 and 11, the multimodality imaging phantom (1) comprises a container (10) having walls (12) allowing a use of the imaging apparatus (not shown) for imaging the interior (14) thereof. The walls (12) are provided with an inlet (16) and an outlet (18).

Figure 4:
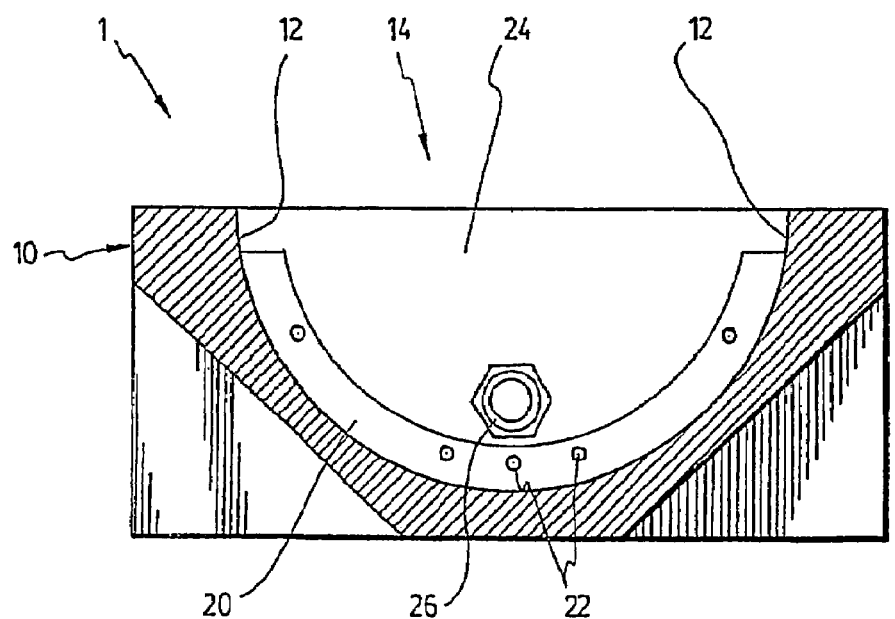
FIG. 4 is a cross-sectional view taken along line IV-IV of the phantom shown in FIG. 3.

As shown in FIG. 4, the phantom (1) also comprises a first layer (20) of tissue mimicking material located in a portion of the interior (14) of the container (10). At least one marker (22) is embedded in the first layer (20). The markers (22) have an acoustic impedance that is 3 to 30 times higher than that of the first layer (20), an X-ray absorption coefficient that is 3 to 50 times higher than that of the first layer (20), and a MR (magnetic resonance) axial relaxation time that is 2 to 20 times lower than that of the first layer (20). In accordance with a preferred embodiment of the invention, the markers (22) have an acoustic impedance that is 10 to 15 times higher than that of the first layer (20), an X-ray absorption coefficient that is 10 to 20 times higher than that of the first layer (20), and/or a MR axial relaxation time that is 4 to 7 times lower than that of the first layer (20). Preferably, the MR axial relaxation time is a longitudinal relaxation time $T_1$.

Figure 2:
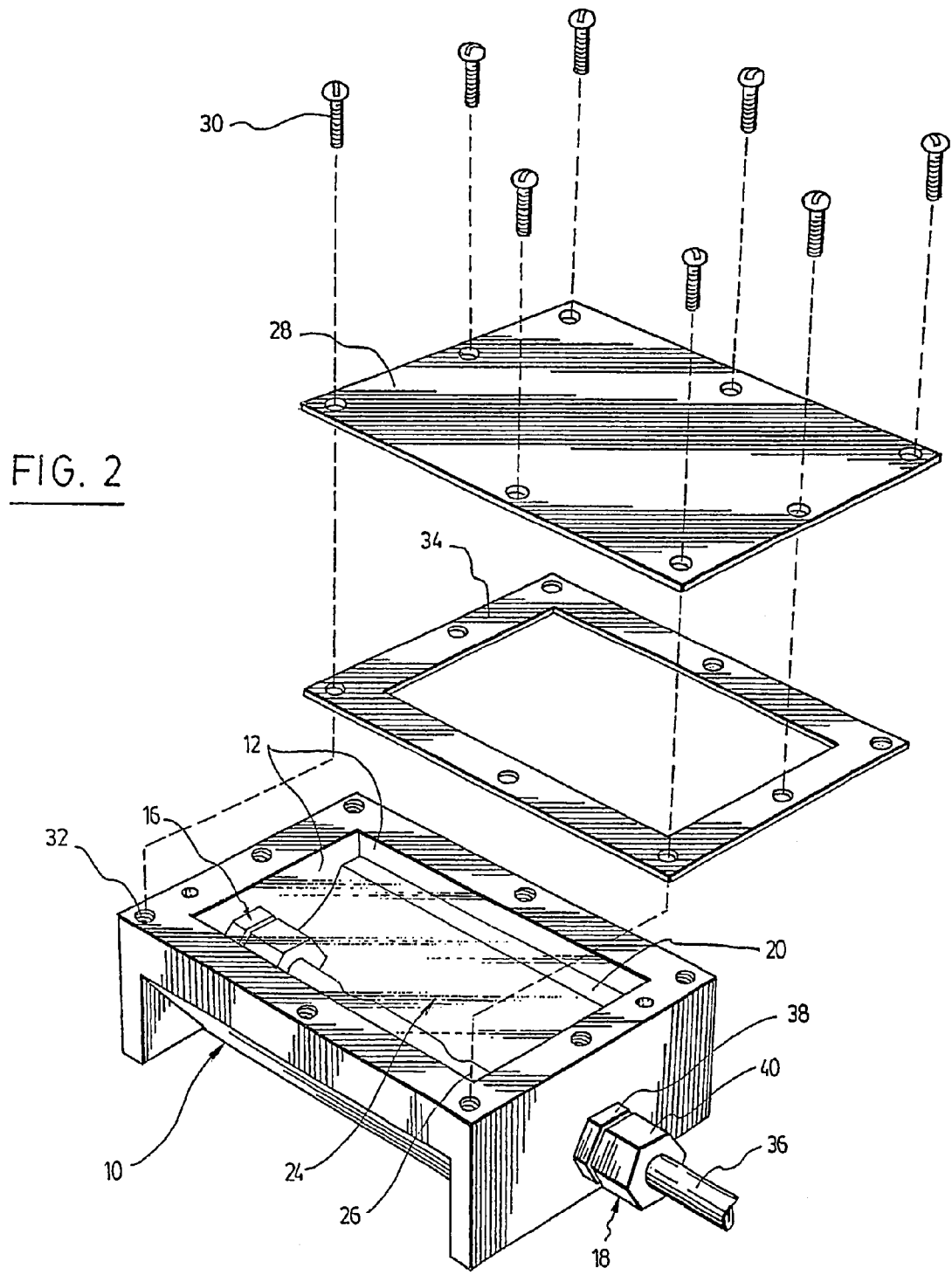
FIG. 2 is a exploded perspective view of parts of a phantom according to the invention.
Figure 11:
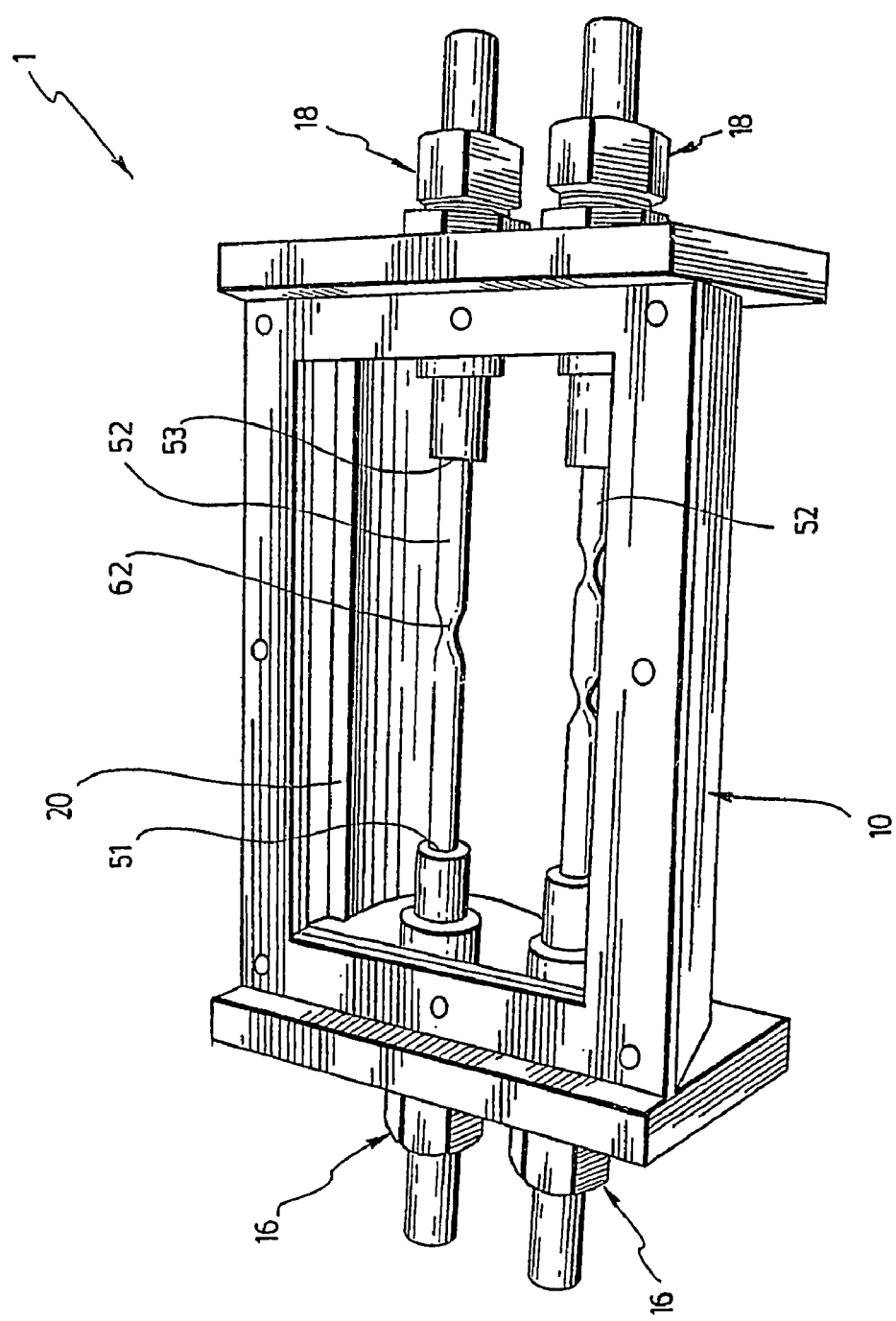
FIG. 11 is a perspective view of a phantom according to another embodiment of the invention, with simulating pieces mounted therein.

Referring more particularly to FIGS. 2 and 4, the phantom further comprises a second layer (24) of tissue mimicking material located in a remaining portion of the interior (14) of the container (10). A vessel (26) is embedded in the second layer (24) and is operatively connected to the inlet (16) and the outlet (18). The inlet (16) and the outlet (18) are used for connecting the vessel (26) to external devices (not shown) such as a pump to generate fluid circulation inside the vessel (26). The circulation of the fluid in the vessel (26) advantageously mimics the blood circulation. The fluid can also be static in the vessel (26). The phantom (1) can comprise more than one vessel and consequently more than one set of inlet (16) and outlet (18) as illustrated on FIG. 11. The vessel (26) can also be a bifurcation connected to an inlet (16) and to outlets (18), and the phantom (1) can comprises one or more bifurcations. In FIG. 11, the inlets (16) of the sets are located on a same side of the container (10). It should be understood that the inlets (16) and outlets (18) can be mounted so as to produce a liquid circulation in the vessels (26) in opposite directions if desired.

The multimodality imaging phantom is particularly useful for calibrating devices for imaging vascular conduits. The phantom is compatible with X-ray, ultrasound and magnetic resonance imaging techniques. It allows testing, calibration, and inter-modality comparative studies of imaging devices, in static or dynamic flow conditions. It also provides a geometric reference for evaluation of accuracy of imaging devices. A vessel (26) of known desired geometry runs throughout the second layer (24) and is connected to an inlet (16) and outlet (18) at its extremities for generating a flow circulation in the vessel (26). The phantom also contains at least one fiducial marker (22) detectable in the modalities: X-ray, ultrasound and magnetic resonance. The markers (22) are implanted at precise known locations to allow identification and orientation of plane views, and it can be used for calibration, resealing and fusion of 3D images obtained from different modalities, and 3D image reconstruction from angiographic plane views.

Composition of the first and the second layers (20 and 24) as well as the markers (22), are selected so that they meet two major requirements: firstly, materials used to manufacture the first and the second layers (20 and 24) should create no or a minimum of artifacts on images in any modality, and secondly, the marker (22) should be easily detected and identified on images obtained from all the modalities, so that they can be properly used for 3D reconstruction or multimodality image fusion. The markers (22) appear clearly on phantom images when there is high contrast between them and the material in which they are inserted, i.e. the first layer (20). This means that the markers (22) must have different characteristics than those of the material of the first layer (20). Tissue-mimicking material of the first layer (20) and the markers (22) are chosen so as to provide such contrast in all the modalities for which the phantom is designed to be used. The use of solid markers is preferred since it prevents the risk of diffusion into the surrounding material of the first layer (20), which can happen when using a liquid marker consisting in a fluid (for example MRA contrast agents such as gadolinium, X-ray contrast agent such as iodine and ultrasound contrast agent such as encapsulated gas bubbles) introduced in sealed cavities into the material of the first layer (20).

To obtain the differential characteristics between the markers (22) and the first layer (20), it is preferred to use markers (22) made of glass and a tissue mimicking material of the first layer (20) containing at least one fat component. The at least one fat component is preferably an oil which is advantageously a paraffinic oil.

According to a preferred embodiment of the invention, the tissue mimicking material of the first layer (20) is a gel of agar containing a paraffinic oil, and the tissue mimicking material of the second layer (24) is a gel of agar. The preferred composition of the first and second layers (20, 24) is given in details below.

Figure 13:
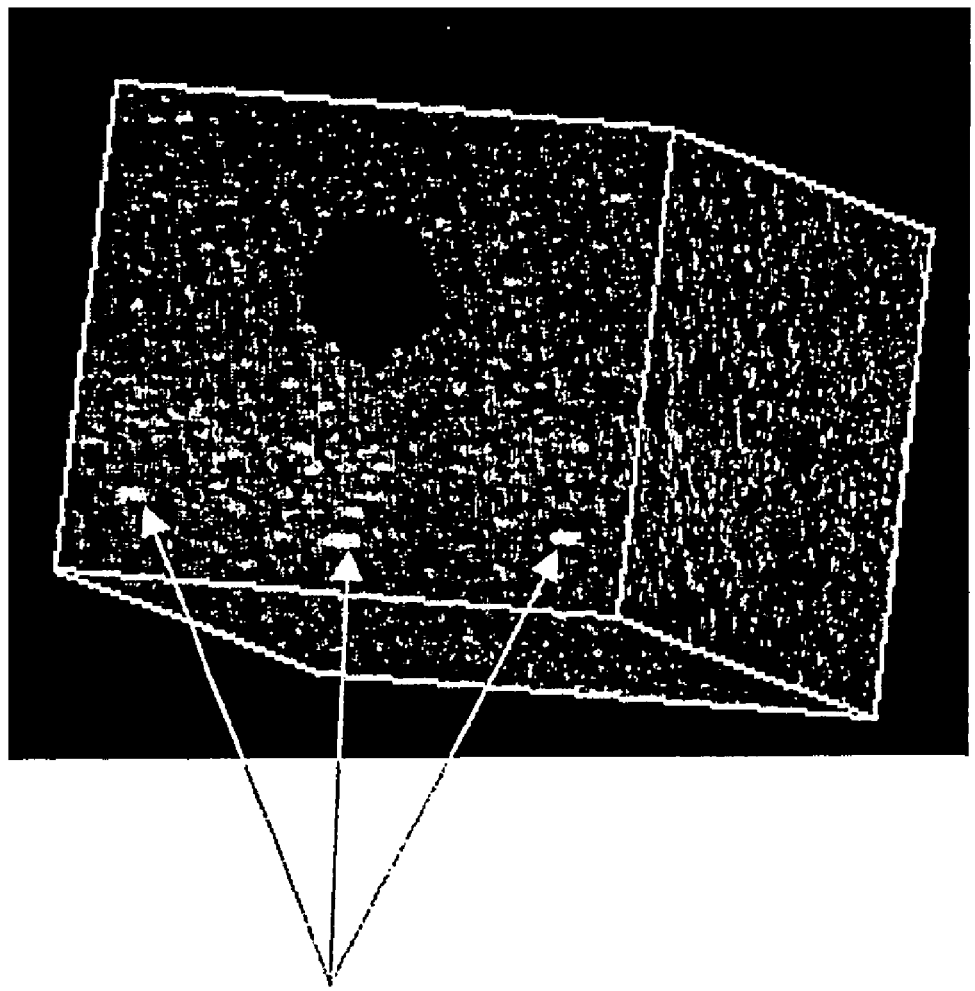
FIG. 13 is a photograph of a perspective view of a portion of the phantom of FIG. 12 taken with a B-mode ultrasound apparatus.

In acoustic imaging (ultrasonography), contrast between two adjacent materials results from a difference of acoustic impedance. Agar gels are known to have an acoustic impedance of about $1.5 \times 10^5$ g/cm$^{-2}$ s$^{-1}$. For a mixture of agar gel with oil, the acoustic impedance is in the range of 1.5 to $1.8 \times 10^5$ g/cm$^{-2}$s$^{-1}$. Therefore, as far as acoustic imaging is concerned, fiducial markers (22) could be made of any material having a much greater impedance, for them to be clearly seen, for example ten times. On the other hand, the material of the fiducial markers (22) should not have a too high mismatch in acoustic impedance to avoid exaggerated attenuation and shadowing behind the markers. In a preferred embodiment of the invention, glass balls which have an impedance of $14.5 \times 10^5$ g/cm$^{-2}$ s$^{-1}$, are used as markers (22). They appear as white bright circles on B-mode ultrasound images as shown in FIG. 13.

Figure 12:
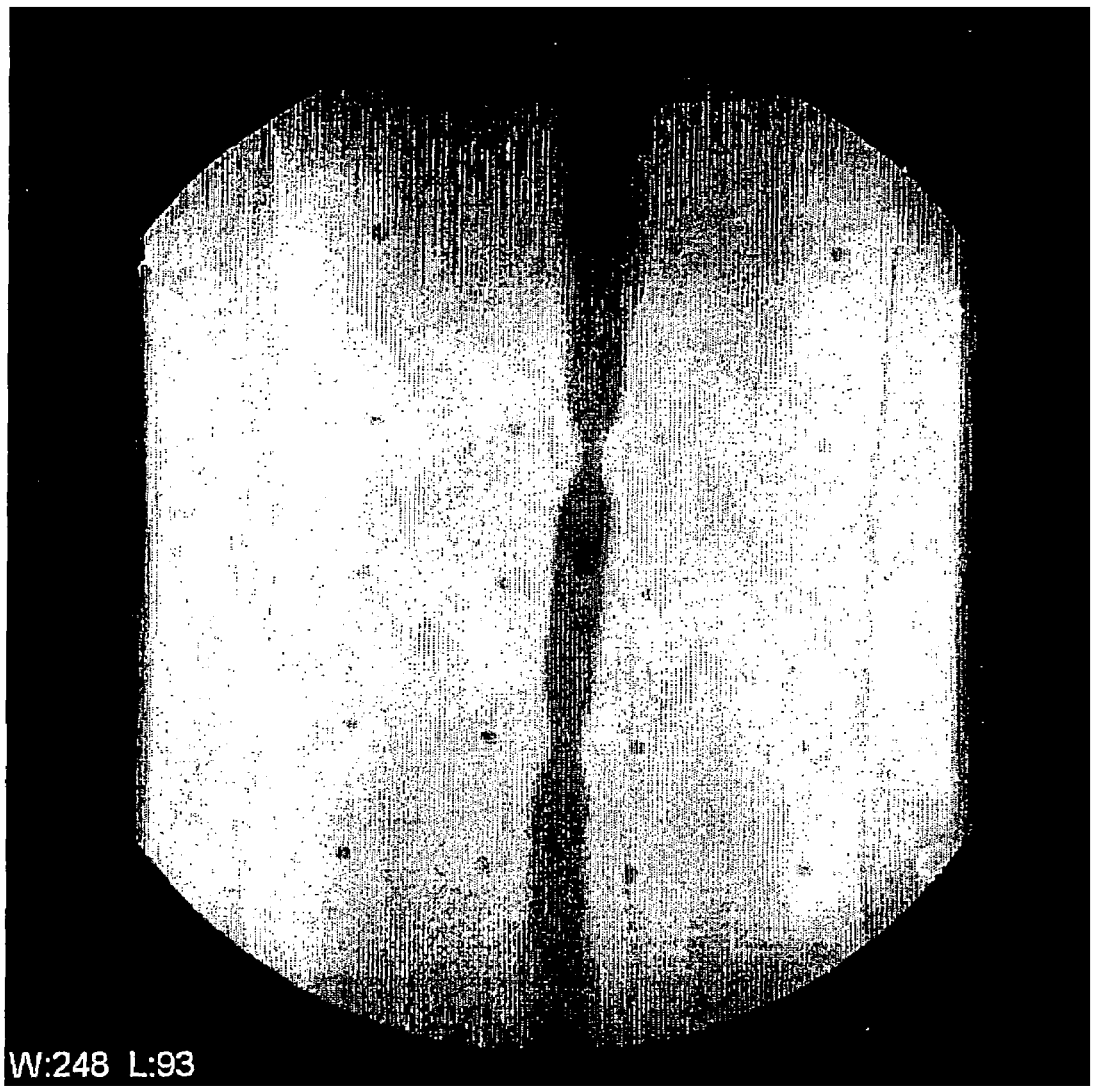
FIG. 12 is a photograph of a top view of a phantom according to the invention taken with a digital subtraction X-ray angiography apparatus at zero cranio-caudal or lateral angulation.
Figure 14:
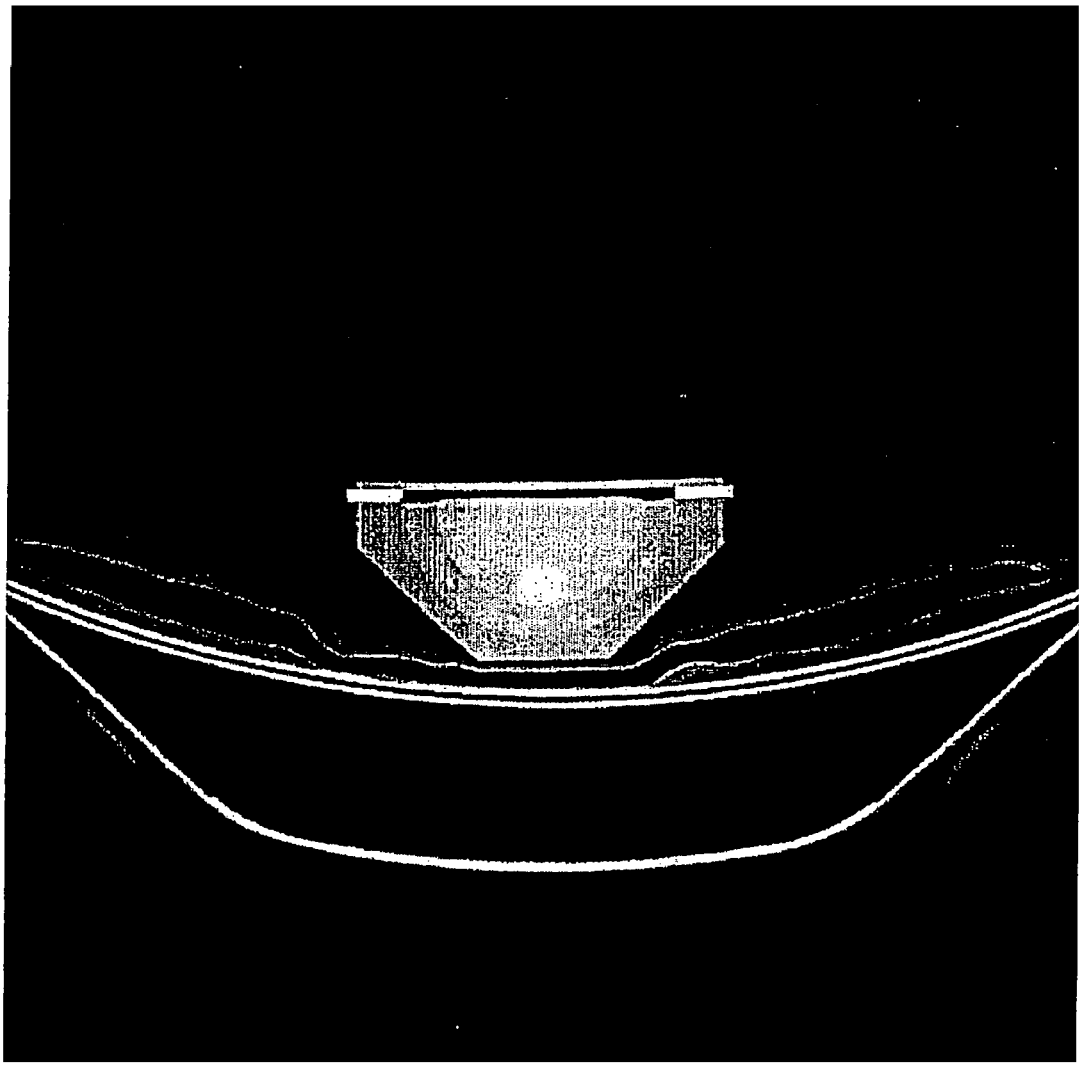
FIG. 14 is an image of a cross-sectional view of the phantom of FIG. 12 taken with a X-ray computerized tomography scanner.

For imaging techniques based on X-ray such as X-ray angiography and computerized tomography, contrast on the images will result from a difference in X-ray absorption of the different materials. The absorption coefficient of different kinds of glasses is ranging from 1 to 10 cm$^{-1}$ and the one of a gel of agar with paraffinic oil is about 0.24 cm$^{-1}$ at 90 kVp. Consequently, materials like glass, which have an absorption coefficient significantly higher than that of a gel of agar will appear clearly both in digital angiography and CT images, as can be seen on FIGS. 12 and 14, respectively. Distortion in the image of FIG. 12 is due to the imaging apparatus.

For magnetic resonance imaging, contrast is essentially based on the difference of relaxation times. The relaxation times comprise the longitudinal relaxation time $T_1$ and transverse relaxation time $T_2$. Medical images are usually $T_1$-weighted, i.e. that the contrast between two tissues results from the difference between their respective values of $T_1$. As the recovered spin-echo signal is a decreasing function of $T_1$, materials with low longitudinal relaxation time appear as bright on $T_1$-weighted images. In the preferred embodiments of the invention, metallic markers could not be used because they create artifacts which prevent from precise determination of the center of the markers on images. Small glass balls are preferred since they are compatible with MRA in addition of being a good selection for ultrasound and X-ray. However, it is important to understand that the magnetic resonance signal level from the agar gel is low, and not very different from that of glass for which the relaxation time $T_1$ is about 1000-1200 ms. Thus, glass markers can not easily be detected when inserted in agar gel alone. Based on the article of Bottomley et al. (Bottomley P. A., Foster T. H., Argersinger R. E., Pfeifer L. M.—A Review of Normal Tissue Hydrogen NMR Relaxation Times and Relaxation Mechanisms: Dependence on Tissue Type, NMR Frequency, Temperature, Species, Excision, and Age, Med. Phys. 1984, 11:425-448), relating to adipose tissues on medical images, fat components are known to have low values of $T_1$ which range from about 200 to about 500 ms, and provide a high contrast on MRA. Therefore, oil has been added into the agar-based gel layer (20) in which markers (22) are inserted. The signal level of the oil-agar gel mixture is then much higher, and the fiducial glass markers (22) thus appear as black circles, hypo-signal, on a light-gray background, as it can be seen in FIG. 15.

Figure 3:
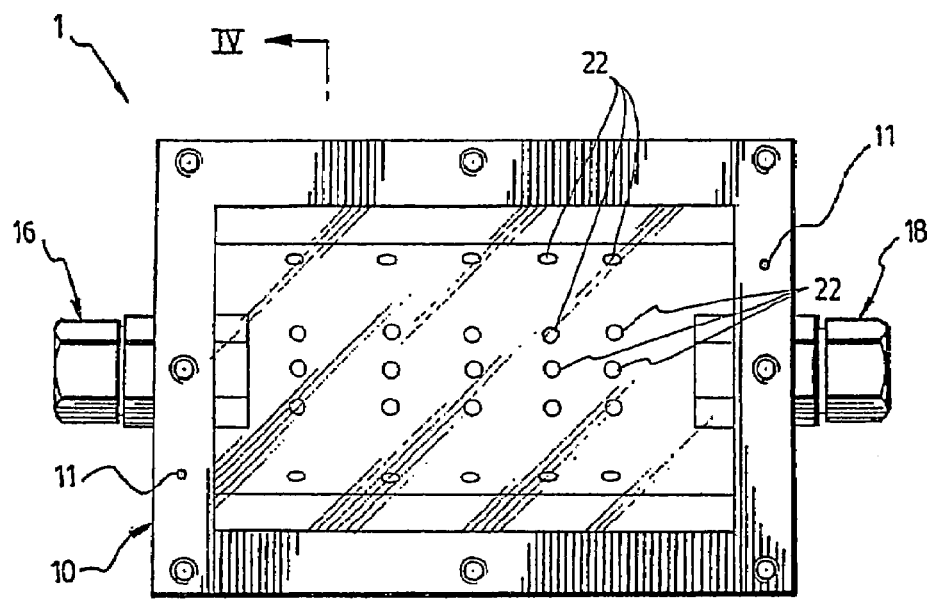
FIG. 3 is a top view of a phantom according to the invention.

Referring to FIGS. 2, 3 and 4, the container (10) of the phantom is preferably made of polyethylen and the interior (14) has a semi-cylindrical shape. In the preferred embodiment illustrated in FIG. 2, the diameter of the semi-cylindrical cavity is 4 inches (101.6 mm) and its length is 9 inches (228.6 mm). The first layer (20) is preferably molded in the container (10) so as to have a semi-cylindrical shape of controlled thickness as detailed herein below. According to the preferred embodiment of the invention illustrated in FIG. 4, the remaining portion of the container (10) is filled with an agar-based gel (the second layer 24) with a semi-cylindrical shape at the bottom superimposed on the first layer (20) of the agar-oil mixture.

Advantageously, several markers (22) of known diameter are implanted at precise known positions and depths in the first layer (20) before the application of the second layer (24). The markers (22) are to be used as fiducial geometrical markers for the purpose of calibrating medical imaging apparatuses, but also in reconstruction of 3D images from plane angiographic views. They also provide a tool for aligning, resizing and fusing the images obtained from the different modalities. More preferably, twenty-five markers (22) are inserted at non-symmetrical positions as shown in FIG. 3. Each marker (22) is a glass ball of 3 mm in diameter and is implanted at a controlled angular position and depth, 6 mm as a preference, from the upper surface of the first layer (20) as illustrated in FIG. 4. The twenty-five markers (22) are divided in five sets of five markers (22) each, see FIG. 3. For each set, the five markers (22) are contained in cross-sectional and longitudinal planes of the container (10). One set is placed in the central axis, and the two sets on both sides are placed at non-symmetrical distances so as to facilitate the determination of the phantom orientation on medical images, especially on angiographic images. For the same reason, in each cross-sectional planar set, the markers (22) are implanted at non-symmetrical positions on either side of the symmetry axis. Said fiducial markers (22) have two functions. Firstly, as they are implanted at precise known locations in the phantom (1) and have a known diameter, they provide a calibration tool for the evaluation of image deformation or distortion inherent to the imaging apparatuses. They can also be used in 3D reconstruction techniques from plane angiographic images, as a basis for the calculation of the parameters of the planar projection associated to each view. Secondly, the markers (22) have been positioned in the phantom (1) so that they can be individually identified on images acquired by any modality. Because different axial and radial distances were selected to position the markers (22), this can be achieved by measuring the distance between markers (22) in the neighborhood. They thus provide a way of aligning images obtained from different modalities, which is necessary for correct comparison, resizing and fusion of said images.

According to a preferred embodiment of the invention, the vessel (26) is made by a lost-material casting technique. Advantageously, the lost-material casting technique uses a low melting point metallic alloy being preferably a cerollow alloy. Such technique is described herein below.

Referring more particularly to FIG. 2, the top of the container (10) is closed by a cover (28) consisting in a polyethylen sheet. The cover (28) is secured to the container (10) by means of a series of eight nylon screws (30) introduced in threaded holes (32) made in the lateral walls (12) of the container (10). Securing the cover (28) is performed in a water bath to prevent air bubbles from remaining between the second layer (24) and the cover (28). Further air ingression inside the phantom is prevented by a rubber gasket (34) installed between the cover (28) and the container (10) to assure a perfect seal. The phantom needs to be protected from air to avoid drying out of the agar-based gel and proliferation of micro-organisms. Moreover, the cover (28) allows to pressurize the fluid inside the vessel (26) and prevent the breaking of the second layer (24), more particularly when the second layer (24) is made of a gel of agar. It should be understand that the container (10) and the cover (28) of the phantom may be made of any material compatible with all imaging techniques. Advantageously, they are made of polyethyen, which does not generate artifacts in any modality.

According to the preferred embodiment of the invention illustrated in FIG. 2, the vessel (26) runs longitudinally all through the second layer (24) and is connected to the inlet (16) and outlet (18) which are preferably located at both extremities of the container (10). Each of the inlet (16) and the outlet (18) advantageously comprises a tubing (36) for connection to the vessel (26). Such tubing (36) is preferably a garolite tubing. Garolite is a material made of a continuous-woven glass fabric laminated with an epoxy resin. Other non-porous and non-metallic materials such as glass or acrylic may be used, with no major imaging problem since the inlet (16) and outlet (18) are preferably located at the extremities of the phantom, outside the region of interest for imaging. The tubing (36) is inserted in polypropylene bulkhead unions (38) screwed in the walls (12) of the container (10) and are secured by bolting the lock-nuts (40) of the bulkhead unions (38). The inlet (16) and outlet (18) provide a means for connecting the phantom to external devices (not shown) such as a pump to circulate blood mimicking fluid inside the vessel (26), and to use contrast agents when required for a good quality imaging. To avoid possible diffusion of the contrast agent into the second layer (24), a thin impermeable material is provided at the external surface of the vessel (26) as a wall between the second layer (24) and the fluid. Such thin impermeable layer is preferably made of latex layer. Connections with devices generating fluid circulation can also be used to study physiological flow conditions inside the phantom. The tubing (36) of the inlet (16) and outlet (18) have the same inner diameter as that of the vessel (26), thus ensuring a smooth geometric transition between the lumen of the vessel (26) and the tubing (36). This has the advantage of minimizing perturbations of the flow that would result from any tubing diameter mismatch.

Referring now to FIG. 1, for imaging with an apparatus using ultrasonography, the phantom (1) is preferably provided with a removable basin (42) on top thereof. The basin (42) has sides which are preferably formed by a rectangular-shaped wall (44) made in one piece of plexiglass. For assuring watertightness of the basin (42), the wall (44) is sit on a rectangular rubber seal (46) and press down against the cover (28) so as to squeeze the rubber seal (46) by means of two bars (48) leaning on the wall (44) and being screwed in the container (10) by a screw (50) at each opposite end thereof. It should be understood that the bottom of the basin (42) is embodied by the cover (28). Water is poured in the basin (42) and the extremity of an ultrasonic probe (not shown) of the apparatus using ultrasonography is immersed in the water for imaging. Alternatively, the water can be replaced by an acoustic gel. For ultrasound imaging, it is also important to avoid air pocket under the cover (28). To do so, water is added on top of the second layer (24) until the container (10) is full and then the cover (28) is secured to the container (10). The basin (42) is used only for ultrasound imaging and is removed when the phantom (1) is imaged in any other modality.

Referring now to FIG. 4, according to a preferred embodiment of the invention, the tissue-mimicking material of the second layer (24) is a gel of agar. Such agar gel is composed of 3 weight percent of agar, 8 weight percent of glycerol, 3 weight percent of cellulose particles, and 86 weight percent of degassed water. Glycerol is added to the mixture to increase the acoustic velocity of the gel, so that it is close to the value in living tissues being of 1540 m/s. The cellulose particles, which are preferably the ones bought under the trademark Sigmacell™ of Sigma Chemical, are added as an ultrasound scattering agent to provide better contrast between the vessel (26) and the second layer (24) in B-mode ultrasonic imaging. In a first step for preparing the agar gel, agar, glycerol and water are mixed together. The resulting mixture is stirred and heated until the agar powder is completely dissolved and a clear gelling liquid is obtained. Then, cellulose is added, the mixture is stirred again, and cooled down to the proper temperature for pouring into the container (10) of the phantom (1), i.e. 45° C.

Still according to a preferred embodiment of the invention, the tissue-mimicking material of the first layer (20) is a gel of agar containing a paraffinic oil which is prepared as follows. Firstly, a volume V of a mixture containing 3 weight percent of agar and 97 weight percent of distilled water is prepared. Then a volume ranging between V/2 and V/3 of paraffinic oil is added. The mixture is heated and energetically stirred until the gel-oil emulsion becomes stable, i.e. water and oil do not separate after stirring. No cellulose particle is added. As the agar gel contains a great amount of water, mixing them with a high proportion of oil or fat component can be difficult because of problems of homogeneity of the mixture resulting in the apparition of oil bubbles inside the gel matrix, and, with excessive oil concentration, the resulting mixture may not be able to harden. For these reasons, although high oil concentrations provide better contrast with markers, the proportion of oil included in the preparation of the gel is preferably selected in the range 33-50% in volume.

Accordingly to a preferred embodiment of the present invention, agar-paraffinic oil mixture of the material of the first layer (20) and glass were found to be a suitable set of materials for fulfill the imaging conditions described above i.e. differences of acoustic impedance, X-ray absorption coefficient and MR axial relaxation time. Any other materials and especially other oils or fat components, and other kinds of glass, meeting such imaging conditions, may be suitable for the present invention.

Referring to FIGS. 2 and 4, the present invention is also directed to a process for manufacturing a multimodality imaging phantom for calibrating an imaging apparatus. Such process comprises the following steps (a) to (e).

Step (a) is providing a container (10) having walls (12) allowing a use of the imaging apparatus (not shown) for imaging the interior (14) thereof. The walls (12) are provided with at least one set of inlet (16) and outlet (18) as described above.

Step (b) is providing a first layer (20) containing a first tissue mimicking material in a portion of the interior (14) of the container (10).

Step (c) is embedding at least one marker (22) in the first layer (20) where the at least one marker (22) has an acoustic impedance that is 3 to 30 times higher than that of the first layer (20), an X-ray absorption coefficient that is 3 to 50 times higher than that of the first layer (20), and a MR axial relaxation time that is 2 to 20 times lower than that of the first layer (20).

Step (d) is providing a second layer (24) containing a second tissue mimicking material in the remaining portion of the interior (14) of the container (10).

Step (e) is embedding a vessel (26) in the second layer (24). The vessel (26) is operatively connected to the inlet (16) and the outlet (18) of the container (10).

Referring now to FIGS. 2, 4, 9, 10 and 11, for providing the second layer (24) and embedding the vessel (26) therein, the steps (d) and (e) preferably comprise the following sub-steps (i) to (vi).

Figure 9:
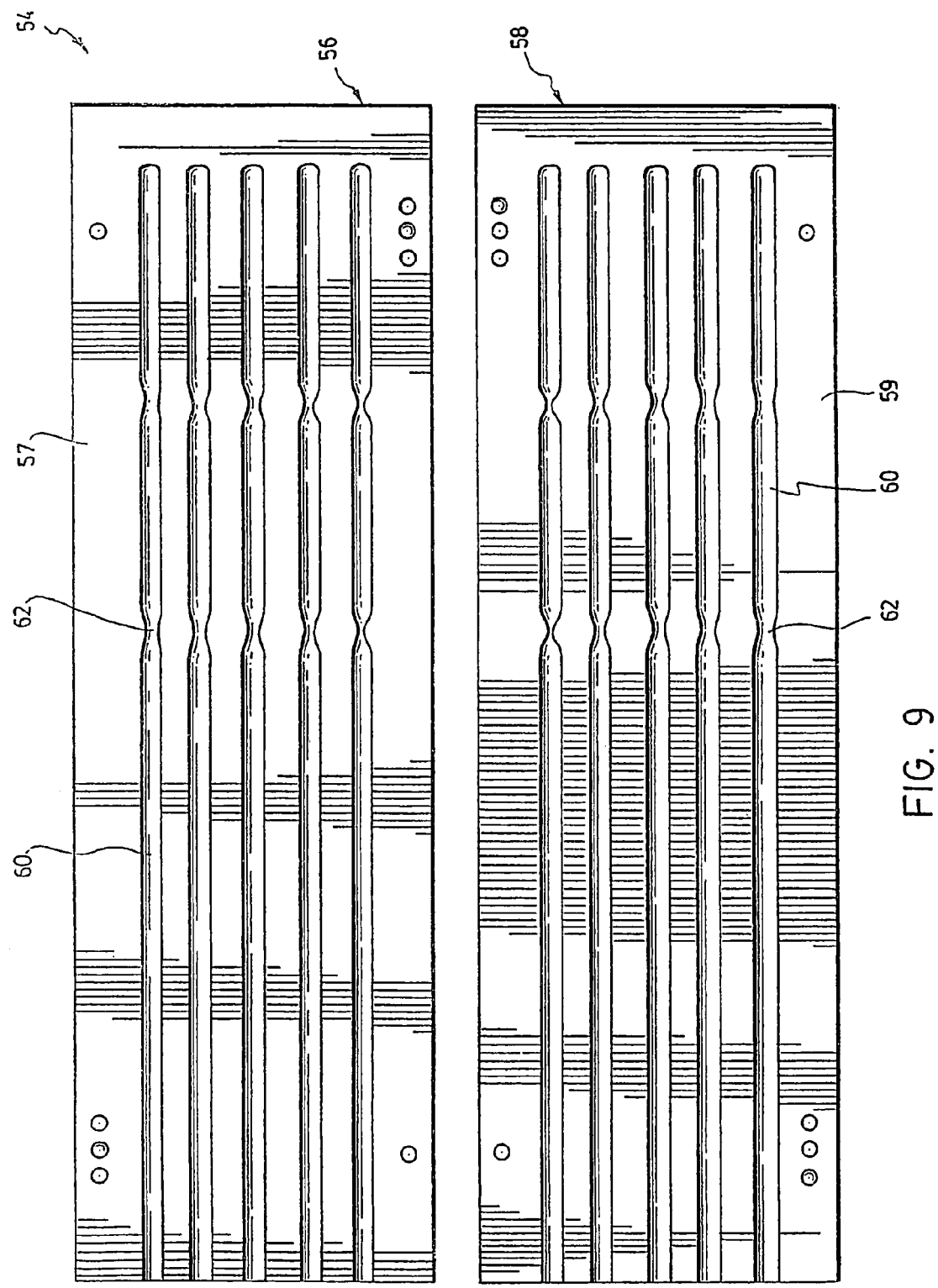
FIG. 9 is a top view of a two-part mold for preparing five pieces simulating vessels with different stenoses.
Figure 10:
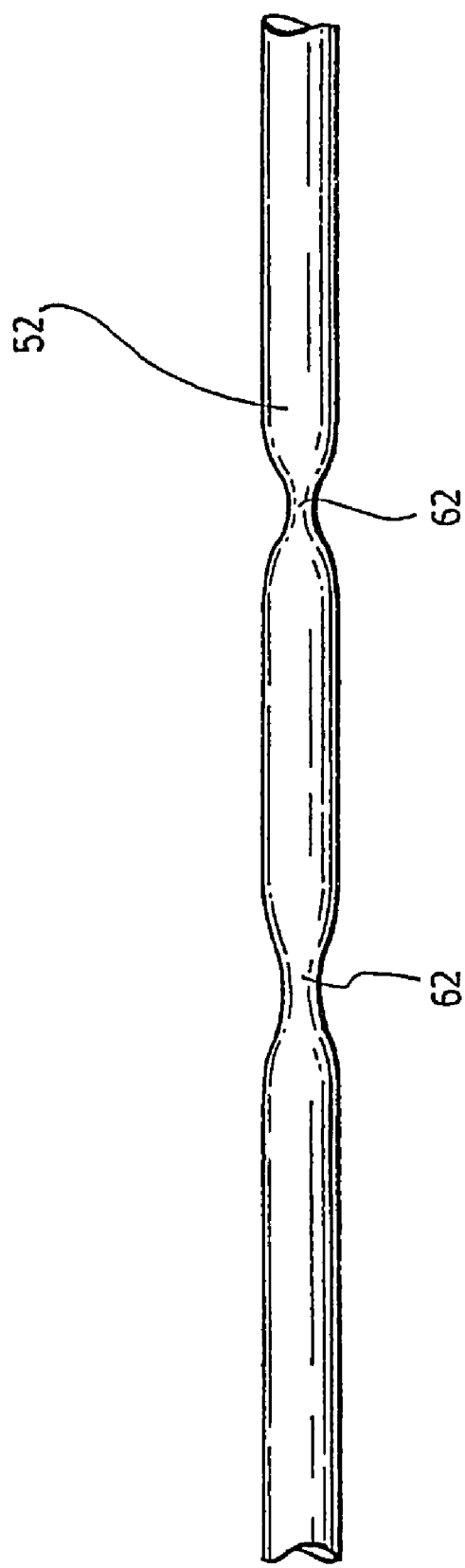
FIG. 10 is a simulating piece prepared by using the mold illustrated in FIG. 9.

Sub-step (i) is molding a simulating piece (52). In FIG. 11, two simulating pieces (52) are installed in the phantom (1) and the second layer (24) is not provided yet. The simulating piece (52) has an exterior shape simulating the vessel (26) to be formed. The simulating piece (52) is made of a molding material having a melting point lower than the melting point of the second tissue mimicking material. In a preferred embodiment of the invention, the molding material is a cerollow alloy which is preferably a cerro-indium alloy having the trademark Cerrolow 136™ sold by Cerrometal Products, Bellefonte, Pa., USA and having a melting point of 58° C. The simulating piece (52) is prepared by pouring the molding material in a liquid state in the aluminium mold (54) shown in FIG. 9. The mold (54) is made of two parts (56 and 58) that fit over each other. The interior face (57 and 59) of each part (56 and 58) of the mold (54) is shown in FIG. 9 as well as the half of five cavities (60) for pouring the molding material and forming five simulating pieces (52). After casting, the cerollow alloy, which is the preferred molding material, is cooled at room temperature for two hours. It is then extracted from the mold (54) and hand-polished to remove surface irregularities as illustrated in FIG. 10. As it can be appreciated in the preferred embodiment of the mold (54) illustrated in FIG. 9, simulating pieces (52) with different stenoses (62) can be prepared. It should be understood that it is possible to prepare a simulating piece (52) of known controlled geometry that simulates any vascular pathologies with no axis of symmetry. For example, one of the simulating pieces (52) shown in the phantom (1) illustrated in FIG. 11 has only one stenosis (62).

Sub-step (ii) is coating the simulating piece with a latex layer. The stimulating piece (52) is previously coated with a thin impermeable material, being preferably a latex layer, at the end of sub-step (i). In such an embodiment, the latex layer forms the wall of the vessel (26) which stays intact after removal of the moten cerollow alloy. This latex layer prevents diffusion into the second layer (24) of a contrast agent used in the fluid.

Sub-step (iii) is connecting one end (51) of the simulating piece (52) to the inlet (16) of the container (10) and another end (53) of the simulating piece (52) to the outlet (18) of the container (10).

Sub-step (iv) is pouring the second tissue mimicking material, while in a liquid state, in the remaining portion of the interior (14) of the container (10) so as to form the second layer (24) and embed the simulating piece (52). FIG. 11 represents the state of a phantom (1) just before executing sub-step (iv).

Sub-step (v) is lowering the temperature of the second tissue mimicking material under its melting point so that the second tissue mimicking material becomes solid.

Sub-step (vi) is melting and removing the simulating piece (52) by heating said simulating piece (52) at a temperature higher than the melting point of the molding material and lower than the melting point of the second tissue mimicking material.

According to a preferred embodiment of the invention, the simulating piece (52) is made of a cerollow alloy and the second tissue mimicking material is made of a gel of agar. In such a preferred embodiment, removing the simulating piece by heating is advantageously performed as follow. After the second tissue mimicking material is solidified and the cover (28) is secured to the container (10), the phantom (1) is heated in a water bath for several hours. The phantom (1) is installed in the water bath so that the inlet (16) and outlet (18) are vertically positioned and not in contact with the bottom of the bath that is kept at 65° C. As the temperature inside the phantom reaches 58° C., the cerollow alloy starts melting out of the phantom (1) via the inlet (16) or the outlet (18) depending which one is underneath. Removal of the molten cerollow alloy creates in the gel an empty conduit having the shape of the initial simulating piece (26). Such conduit is called the vessel (26). Small residual cerollow particles can be removed by injection of water at 65° C. in the vessel (26) with a syringe.

Sub-steps (i) to (vi) are a description of the lost-material casting technique for manufacturing a vessel (26). Other techniques to provide a vessel (26) can be used as any one known in the art. Even a real blood vessel can be used.

Referring now to FIGS. 2, 4, 5, 6, 7, and 8, for providing the first layer (20) and embedding the at least one marker (22) in it, steps (b) and (c) preferably comprise the following sub-steps (vii) to (xvi).

Sub-step (vii) is pouring an amount of the first tissue mimicking material, while in a liquid state, in the portion of the interior (14) of the container (10) mentioned in step (b). The first tissue mimicking material has a melting point. According to a preferred embodiment of the invention, the amount of the first tissue mimicking material that is poured represents between 70% to 90% of the total amount forming the first layer (20).

Figure 5:
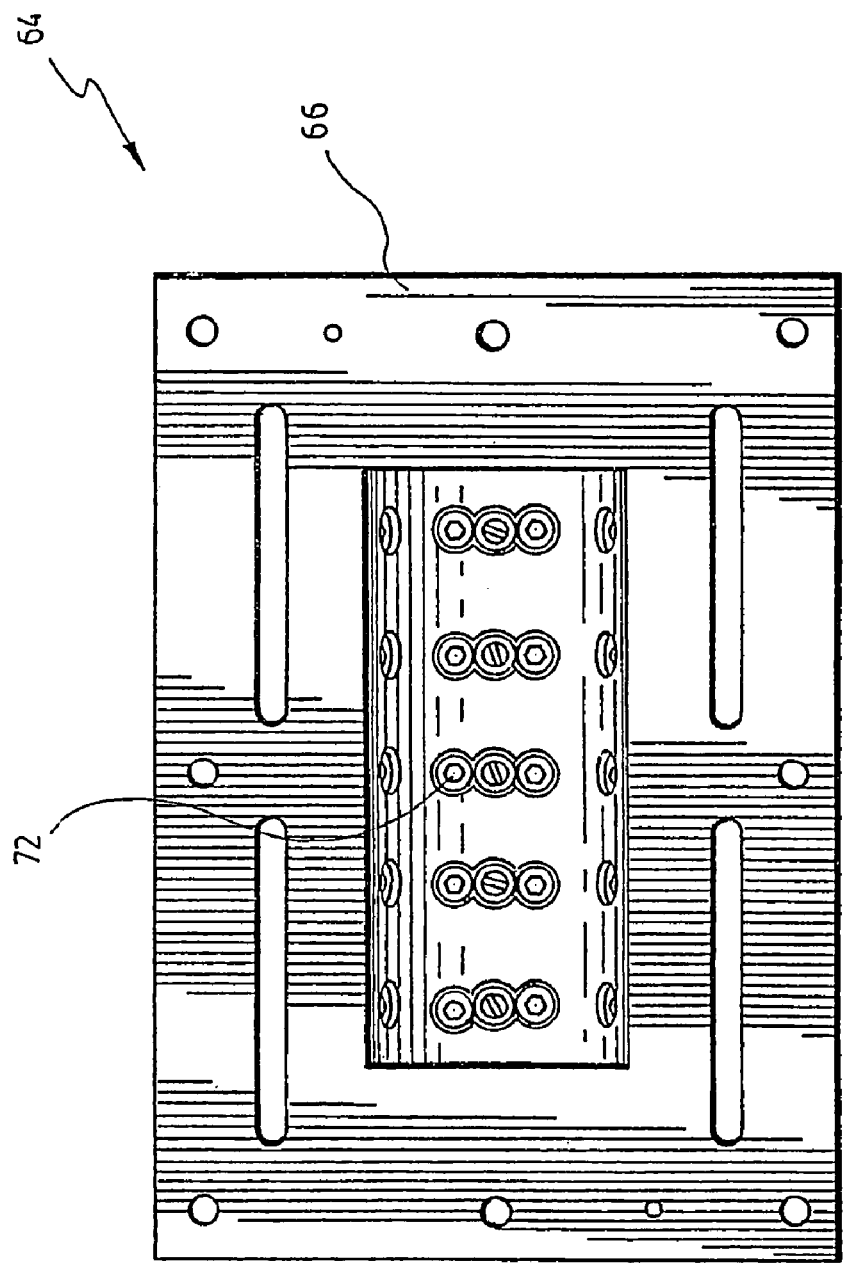
FIG. 5 is a top view of a first template used in a preferred embodiment of the process according to the invention.
Figure 6:
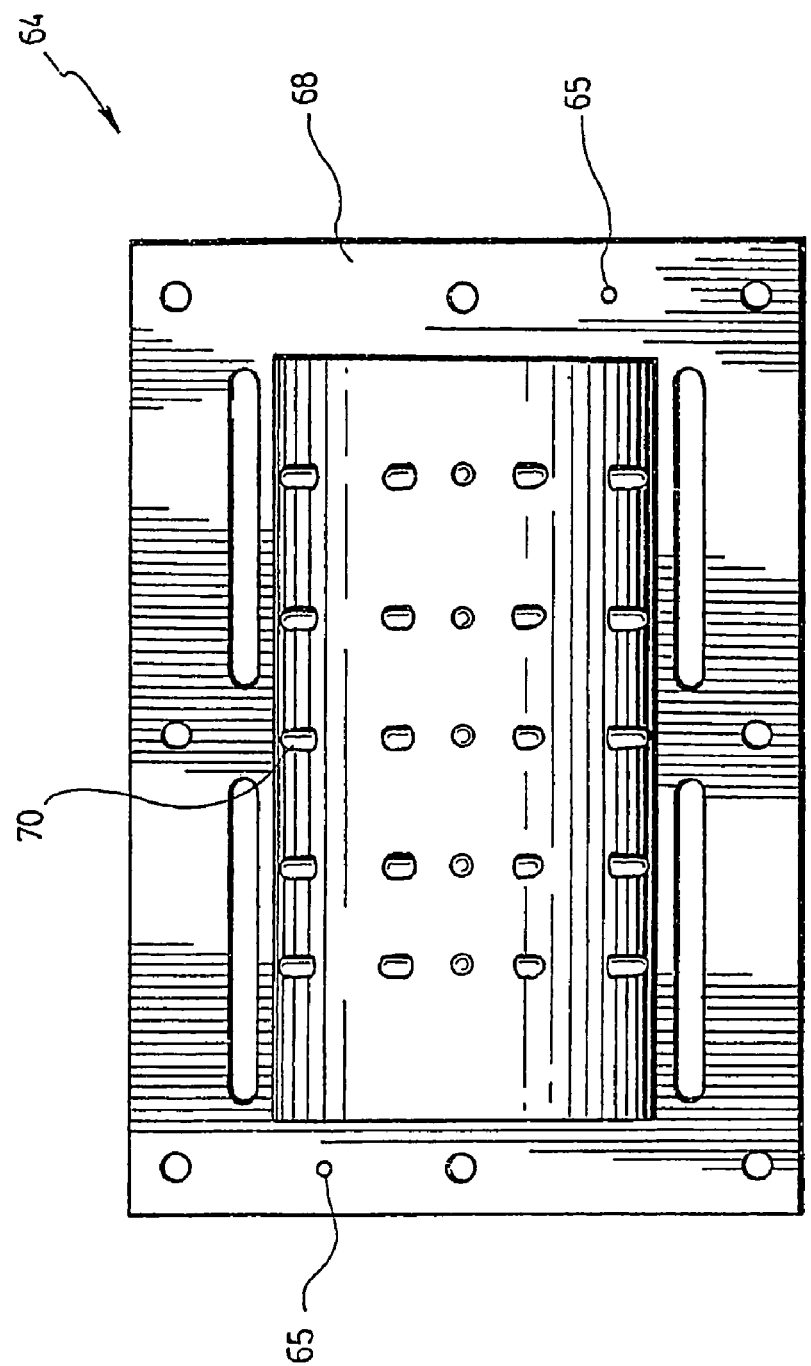
FIG. 6 is a bottom view of the first template illustrated in FIG. 5.

Sub-step (viii) is placing a first template (64) on the amount of the first tissue mimicking material. The top surface (66) and the bottom surface (68) of the first template (64) according to a preferred embodiment of the invention, are illustrated in FIGS. 5 and 6 respectively. As it can be seen from FIG. 6, the bottom surface (68) of the first template (64) has a semi-cylindrical shape. The shape of the first template (64) is designed to follow the interior (14) of the container (10) so that the first tissue mimicking material forms a layer of equal thickness, when solidified. Two alignment pins (65) on the first template (64), shown in FIG. 6, and corresponding holes (11) in the container (10), shown in FIG. 3, ensure a correct positioning of the first template (64) onto the container (10). The first template (64) has at least one pin (70) removably fixed thereto and extending in the first tissue mimicking material. In the preferred embodiment shown in FIG. 6, twenty-five pins (70) extend form the bottom surface (68) of the first template (64). The pin (70) is advantageously a screw and the head screw (72) is shown on the top surface (66) illustrated in FIG. 5.

Sub-step (ix) is lowering the temperature of the first tissue mimicking material under its melting point so that the first tissue mimicking material becomes solid.

Sub-step (x) is removing the at least one pin (70) so as to free at least one recess (not shown) in the solid first tissue mimicking material. According to the preferred embodiment of the pin (70) which is a screw, removing the pin (70) consists in screw off the pin (70).

Sub-step (xi) is placing the at least one marker (22) in the at least one recess respectively. Preferably, the recess has the same shape than the marker (22). Thus according to a preferred embodiment where the marker (22) is a ball of 3 mm of diameter, the recess has a depth of 6 mm, a circular periphery, a width of 3 mm and a round bottom for snugly fitting the marker (22).

Sub-step (xii) is removing the first template (64).

Sub-step (xiii) is pouring another amount of the first tissue mimicking material, while in a liquid state.

Figure 7:
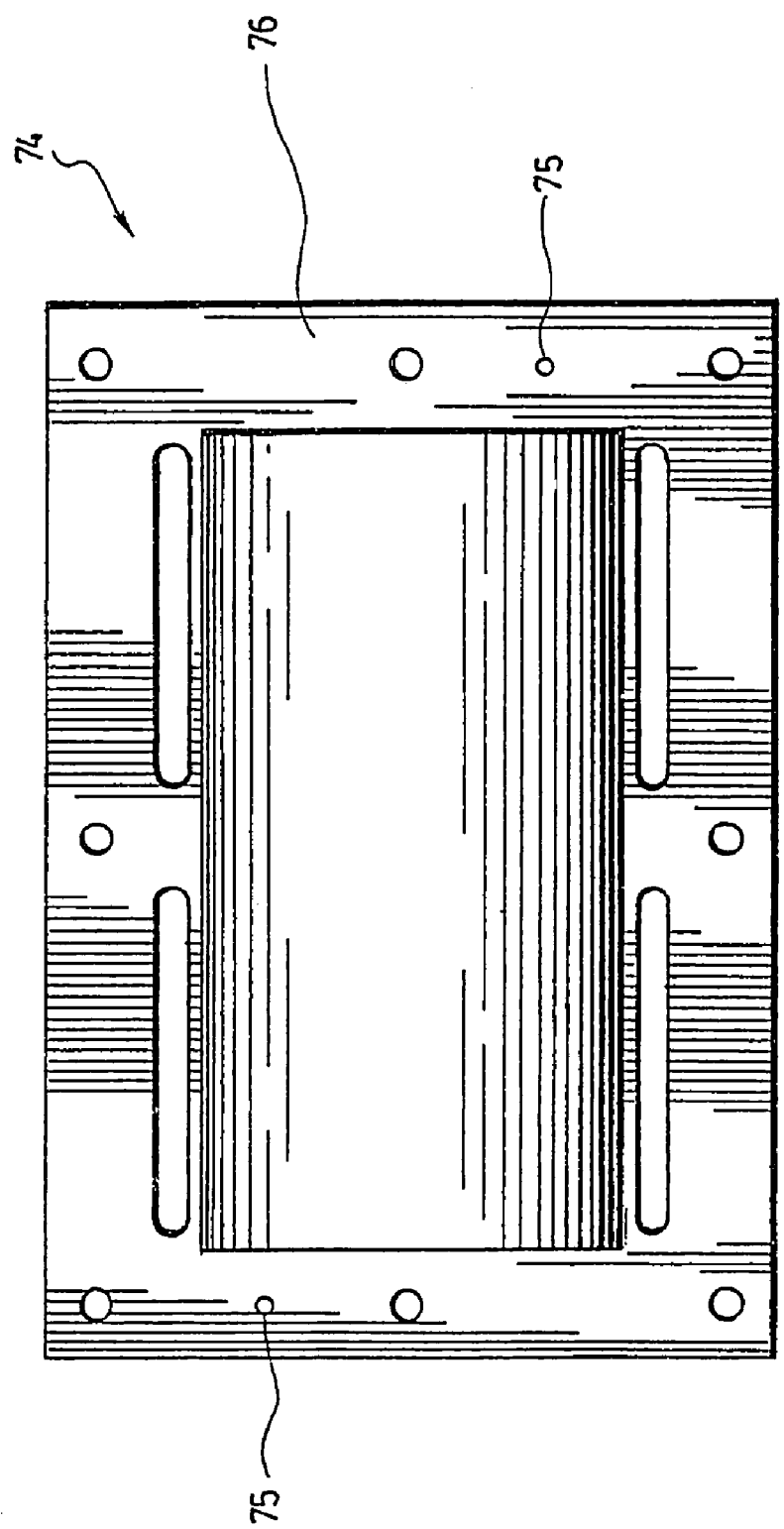
FIG. 7 is a bottom view of a second template used in a preferred embodiment of the process according to the invention.
Figure 8:
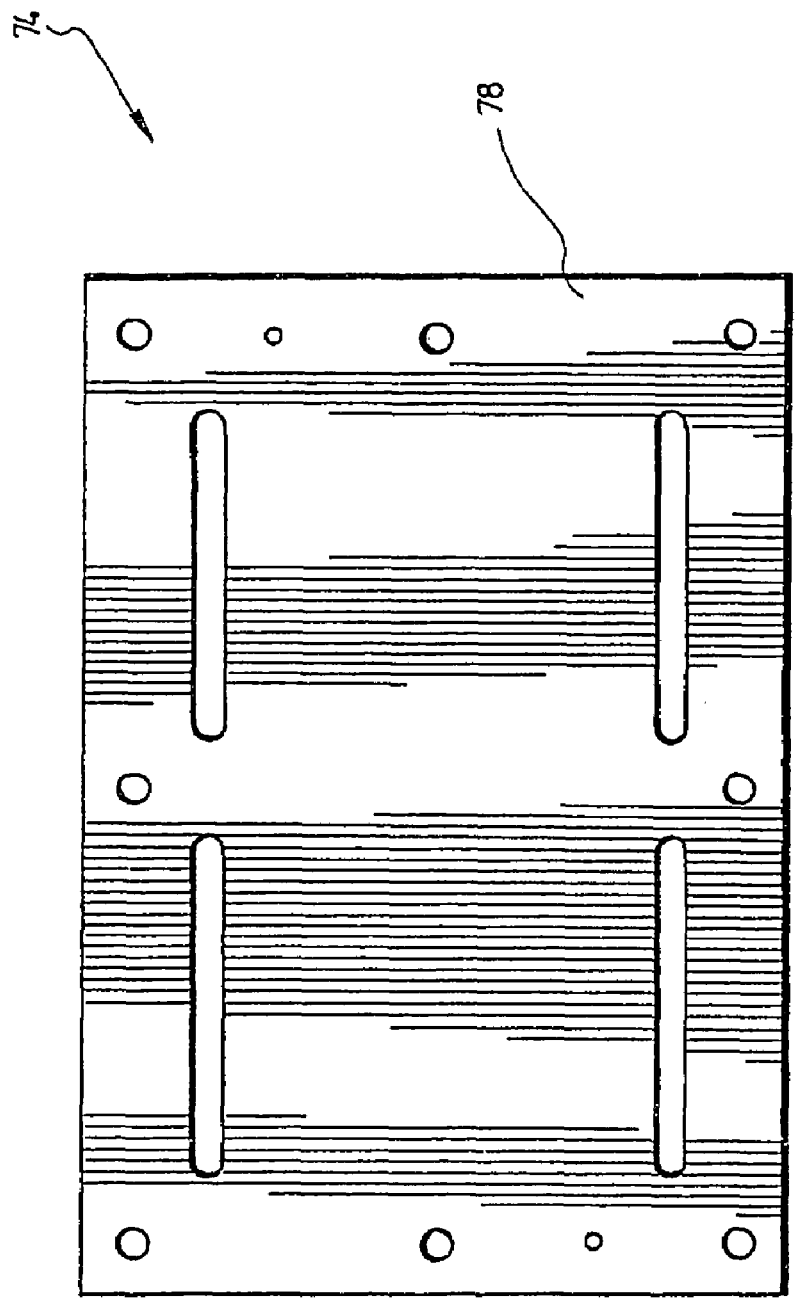
FIG. 8 is a top view of the second template illustrated in FIG. 7.

Sub-step (xiv) is placing a second template (74) on the first tissue mimicking material poured in sub-step (viii) so that the another amount of the first tissue mimicking material covers the at least one marker (22) and fills remaining portion of the at least one recess so as to surround completely the at least one marker (22). The bottom surface (76) and the top surface (78) of the second template (74) according to a preferred embodiment of the invention are illustrated in FIGS. 7 and 8 respectively. As it can be seen from FIG. 7, the bottom surface (76) has a semi-cylindrical shape which is designed to follow the top surface of the solidified amount of first tissue mimicking material and therefore providing a first layer (20) of equal thickness. Two alignment pins (75) on the second template (74) (shown in FIG. 7) and corresponding holes (11) in the container (10) (shown in FIG. 3) ensure a correct positioning of the second template (74) onto the container (10).

Sub-step (xv) is lowering the temperature of the first tissue mimicking material poured in step (xiii) under its melting point so that it becomes solid. After solidification, the two amounts of the first tissue mimicking material cannot be distinguished from one another, both visually and on the acquired images obtained from apparatuses of all modalities.

Sub-step (xvi) is removing the second template (74). Then, the second layer (24) is provided as described above in step (d). According to the preferred embodiment where the second tissue mimicking material is a gel of agar and the molding material of the simulating piece (52) is a Cerrolow 136™, the gel of agar is poured at 45° C. This temperature was found to be a good compromise because it is high enough to allow pouring before solidifying, and it is sufficiently low, compared with the melting point of Cerrolow 136™, to avoid softening and deformation of the simulating piece. The gel of agar is then allowed to solidify at room temperature for approximately 10 hours.

Although preferred embodiments of the invention have been described in detail herein and illustrated in the accompanying drawings, it is to be understood that the invention is not limited to the precise embodiments and that various changes and modifications may be effected therein without departing from the scope or the spirit of the invention.

What is claimed is:

1. A multimodality imaging phantom for calibrating an imaging apparatus, comprising:
   a container having walls allowing a use of the imaging apparatus for imaging the interior thereof, the walls being provided with an inlet and an outlet;
   a first layer of tissue mimicking material located in a portion of the interior of the container;
   at least one marker embedded in the first layer, the at least one marker having an acoustic impedance that is 3 to 30 times higher than that of the first layer, an X-ray absorption coefficient that is 3 to 50 times higher than that of the first layer, and a MR axial relaxation time that is 2 to 20 times lower than that of the first layer; and
   a second layer of tissue mimicking material located in a remaining portion of the interior, the second layer embedding a vessel operatively connected to the inlet and the outlet.

2. The multimodality imaging phantom of claim 1, wherein the MR axial relaxation time is a longitudinal relaxation time $T_1$.

3. The multimodality imaging phantom of claim 1, wherein the at least one marker is made of glass; and the tissue mimicking material of the first layer contains at least one fat component.

4. The multimodality imaging phantom of claim 3, wherein the at least one fat component is an oil.

5. The multimodality imaging phantom of claim 4, wherein the oil is a paraffinic oil.

6. The multimodality imaging phantom of claim 5, wherein the tissue mimicking material of the first layer is a gel of agar containing the paraffinic oil.

7. The multimodality imaging phantom of claim 6, wherein the tissue mimicking material of the second layer is a gel of agar.

8. The multimodality imaging phantom of claim 1, wherein the vessel is made by a lost-material casting technique.

9. The multimodality imaging phantom of claim 7, wherein the vessel is made by a lost-material casting technique using a low melting point metallic alloy.

10. The multimodality imaging phantom of claim 8, wherein the low melting point metallic alloy is a cerollow alloy.

11. The multimodality imaging phantom of claim 1, wherein the phantom comprises several markers at non-symmetrical positions within the first layer.

12. The multimodality imaging phantom of claim 1, wherein the at least one marker has an acoustic impedance that is 10 to 15 times higher than that of the first layer.

13. The multimodality imaging phantom of claim 1, wherein the at least one marker has an X-ray absorption coefficient that is 10 to 20 times higher than that of the first layer.

14. The multimodality imaging phantom of claim 1, wherein the at least one marker has a MR axial relaxation time that is 4 to 7 times lower than that of the first layer.

15. The multimodality imaging phantom of claim 9, wherein the vessel has a wall formed of a latex layer to prevent contrast diffusion.

16. A process for manufacturing a multimodality imaging phantom for calibrating an imaging apparatus, comprising the steps of:
   a) providing a container having walls allowing a use of the imaging apparatus for imaging the interior thereof, the walls being provided with an inlet and an outlet;
   b) providing a first layer containing a first tissue mimicking material in a portion of the interior of the container;
   c) embedding at least one marker in the first layer, the at least one marker having an acoustic impedance that is 3 to 30 times higher than that of the first layer, an X-ray absorption coefficient that is 3 to 50 times higher than that of the first layer, and a MR axial relaxation time that is 2 to 20 times lower than that of the first layer;
   d) providing a second layer containing a second tissue mimicking material in the remaining portion of the interior of the container; and
   e) embedding a vessel in the second layer, the vessel being operatively connected to the inlet and the outlet of the container.

17. The process of claim 16, wherein the steps (d) and (e) comprise the sub-steps of:
   i) molding a simulating piece having an exterior shape simulating the vessel, with a molding material having a melting point lower than the melting point of the second tissue mimicking material;
   ii) coating the simulating piece with a latex layer;
   iii) connecting one end of the simulating piece to the inlet of the container and another end of the simulating piece to the outlet of the container;
   iv) pouring the second tissue mimicking material, while in a liquid state, in the remaining portion of the interior of the container so as to form the second layer and embed the simulating piece;
   v) lowering the temperature of the second tissue mimicking material under its melting point so that the second tissue mimicking material becomes solid; and
   vi) melting and removing the simulating piece by heating said simulating piece at a temperature higher than the melting point of the molding material and lower than the melting point of the second tissue mimicking material.

18. The process of claim 17, wherein the simulating piece is made of a cerollow alloy and the second tissue mimicking material is made of a gel of agar.

19. The process of claim 16, wherein the steps (b) and (c) comprise the sub-steps of:
   vii) pouring an amount of the first tissue mimicking material, while in a liquid state, in said portion of the interior of the container, the first tissue mimicking material having a melting point;
   viii) placing a first template on the amount of the first tissue mimicking material, the first template having at least one pin removably fixed thereto and extending in the first tissue mimicking material;
   ix) lowering the temperature of the first tissue mimicking material under its melting point so that the first tissue mimicking material becomes solid;
   x) removing the at least one pin so as to free at least one recess in the solid first tissue mimicking material;
   xi) placing the at least one marker in the at least one recess respectively;
   xii) removing the first template;
   xiii) pouring another amount of the first tissue mimicking material, while in a liquid state;

xiv) placing a second template on the first tissue mimicking material poured in step (viii) so that the another amount of the first tissue mimicking material covers the at least one marker and fills remaining portion of the at least one recess;

xv) lowering the temperature of the first tissue mimicking material poured in step (xiii) under its melting point so that it becomes solid; and xvi) removing the second template.

20. The process of claim 16, wherein the at least one marker is made of glass and the first tissue mimicking material contains at least one fat component.

21. The multimodality imaging phantom of claim 10, wherein the vessel has a wall formed of a latex layer to prevent contrast diffusion.

22. The multimodality imaging phantom of claim 1, wherein the first layer has a semi-cylindrical shape of controlled thickness, and the second layer has a semi-cylindrical shaped bottom.

23. The multimodality imaging phantom of claim 1, wherein the MR axial relaxation time is a transverse relaxation time $T_2$.

* * * * *